US008942789B2

(12) United States Patent
Ostermeier et al.

(10) Patent No.: US 8,942,789 B2
(45) Date of Patent: Jan. 27, 2015

(54) 2D3D OVERLAY ON A CPR BASIS FOR ANEURYSM REPAIR

(75) Inventors: Martin Ostermeier, Buckenhof (DE); Marcus Pfister, Bubenreuth (DE)

(73) Assignee: Siemens Aktiengesellschaft, Munich (DE)

( * ) Notice: Subject to any disclaimer, the term of this patent is extended or adjusted under 35 U.S.C. 154(b) by 947 days.

(21) Appl. No.: 12/900,082

(22) Filed: Oct. 7, 2010

(65) Prior Publication Data

US 2012/0089003 A1    Apr. 12, 2012

(51) Int. Cl.
*A61B 5/05*     (2006.01)
*A61B 6/00*     (2006.01)
*A61B 6/03*     (2006.01)
*A61B 6/12*     (2006.01)
*G06T 15/08*    (2011.01)
*G06T 19/00*    (2011.01)
*A61F 2/95*     (2013.01)

(52) U.S. Cl.
CPC .............. *A61B 6/5223* (2013.01); *A61B 6/032* (2013.01); *A61B 6/12* (2013.01); *A61B 6/4085* (2013.01); *A61B 6/4441* (2013.01); *A61B 6/487* (2013.01); *A61B 6/488* (2013.01); *A61B 6/504* (2013.01); *A61B 6/5235* (2013.01); *G06T 15/08* (2013.01); *G06T 19/00* (2013.01); *A61F 2/95* (2013.01); *G06T 2210/41* (2013.01); *G06T 2215/06* (2013.01)
USPC ........... 600/427; 600/411; 600/467; 382/130; 382/285; 378/42

(58) Field of Classification Search
CPC ........ A61B 8/00; A61B 5/7554; A61B 6/466; G06T 7/003; G06T 19/00
See application file for complete search history.

(56) References Cited

U.S. PATENT DOCUMENTS

| | | | |
|---|---|---|---|
| 6,782,284 B1 * | 8/2004 | Subramanyan et al. | 600/407 |
| 6,837,892 B2 * | 1/2005 | Shoham | 606/130 |
| 2003/0060703 A1 | 3/2003 | Barrick | |
| 2006/0099558 A1 | 5/2006 | Ema | |
| 2006/0184006 A1 * | 8/2006 | Chen et al. | 600/416 |

(Continued)

FOREIGN PATENT DOCUMENTS

CN    1871998 A    12/2006

OTHER PUBLICATIONS

Armin Kanitsar et al., Diagnostic Relevant Visualization of Vascular Structures, Technical Report TR-186-2-04-02, Jan. 20, 2004, TU Vienna, pp. 1-20.

*Primary Examiner* — Unsu Jung
*Assistant Examiner* — Michael N Fisher
(74) *Attorney, Agent, or Firm* — Schiff Hardin LLP (57) ABSTRACT

In a method for fluoroscopy controlled insertion of a stent into a curved aorta for aneurysm repair, a 3D volume image is obtained of a patient's aorta at the aneurysm. By knowing a registration of the 3D volume image to a C-arm of an angiographic system and projection geometry of the angiography system, the 3D volume images are projected to a 2D fluoroscopy image of the angiography system. For the 2D3D overlay, the 3D volume image is displayed as a curved planar reconstruction in which the 2D fluoroscopy image and the 3D volume image are warped around a curved center line of the curved aorta or around a curved guide instrument center line to correct for the curvature of the aorta so that the previously curved aorta center line or curved center line of the guide instrument turns into a straight line to visualize insertion of the stent.

8 Claims, 9 Drawing Sheets

(56) References Cited

U.S. PATENT DOCUMENTS

| | | |
|---|---|---|
| 2008/0240337 A1* | 10/2008 | Galant et al. .................. 378/4 |
| 2008/0264102 A1* | 10/2008 | Berra ........................... 63/1.11 |
| 2009/0310847 A1* | 12/2009 | Matsuzaki et al. ............ 382/132 |
| 2010/0061611 A1* | 3/2010 | Xu et al. ....................... 382/131 |
| 2010/0128963 A1* | 5/2010 | Waku et al. ................... 382/134 |
| 2010/0131887 A1* | 5/2010 | Salazar-Ferrer et al. ..... 715/788 |
| 2010/0166283 A1* | 7/2010 | Grosskopf .................... 382/131 |
| 2010/0215225 A1* | 8/2010 | Kadomura et al. ........... 382/128 |

* cited by examiner

2D3D OVERLAY ON A CPR BASIS FOR ANEURYSM REPAIR

BACKGROUND

This disclosure relates to the prior art fields of registration of 2D and 3D images; CPR visualization of vessels; and localizing catheters and guide wires (or other instruments) in 2D images.

More particularly this disclosure relates to the prior art field of fluoroscopy controlled, interventional repair of Abdominal Aortic Aneurysms (AAA), which is a disease of the abdominal aorta. See prior art FIGS. 1A,B,C. This disease is usually treated by inserting stent grafts 10 into the aorta 11 to remodel the organ. Through the groin arteries 13, guide wires 12 and catheters are inserted through which one or more stent grafts 10 are placed (FIGS. 1A,B,C).

Important for the delivery of these grafts is to stay in a determined "landing zone". The object is to place the stent in a healthy area without occluding any important vessel branches, like e.g. the renal arteries. A sensitive point during the intervention is the release of the main stent in the aorta (FIG. 1C). Sometimes the finite stent must be mounted from different stent parts, e.g. from stents covering the leg arteries, the aorta etc.

Figure 1:
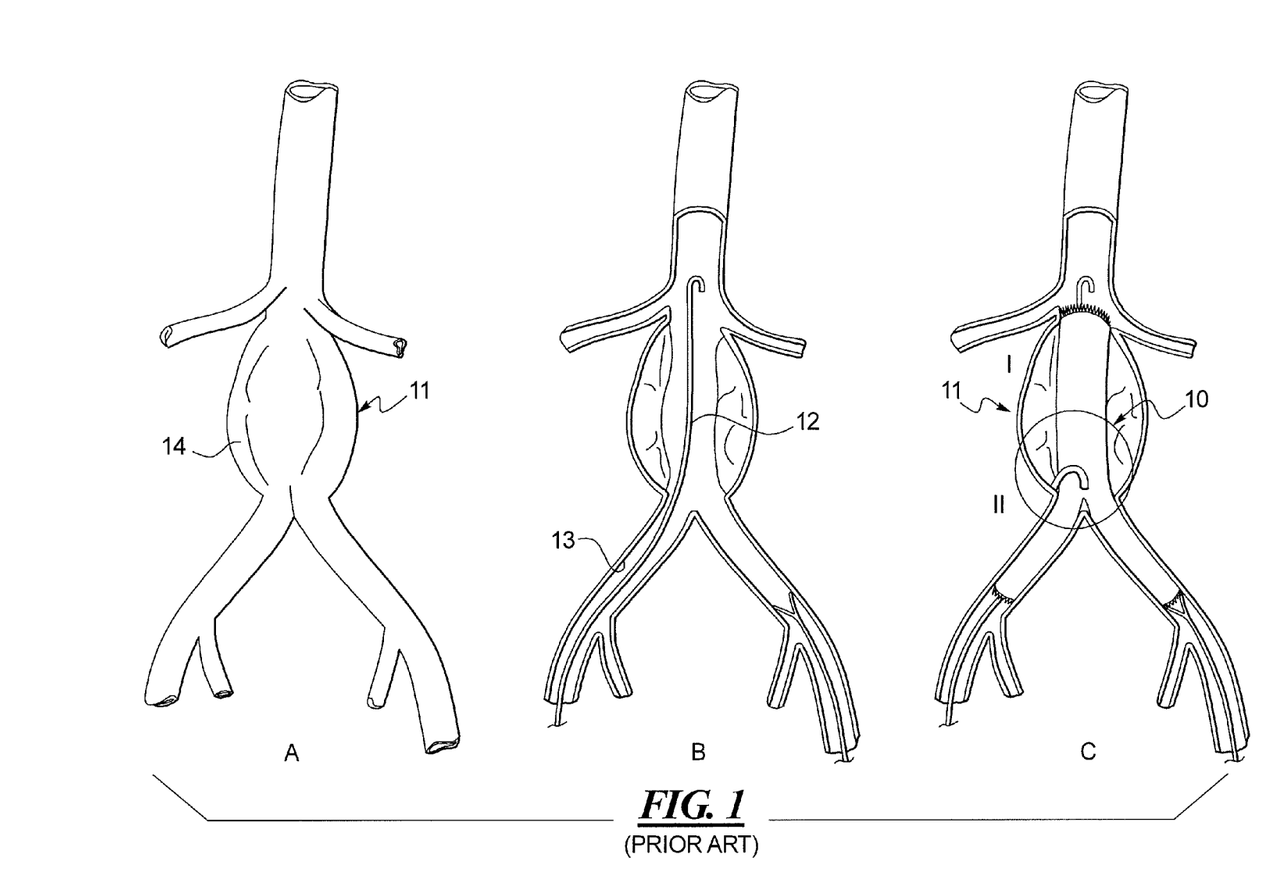
Figure 2:
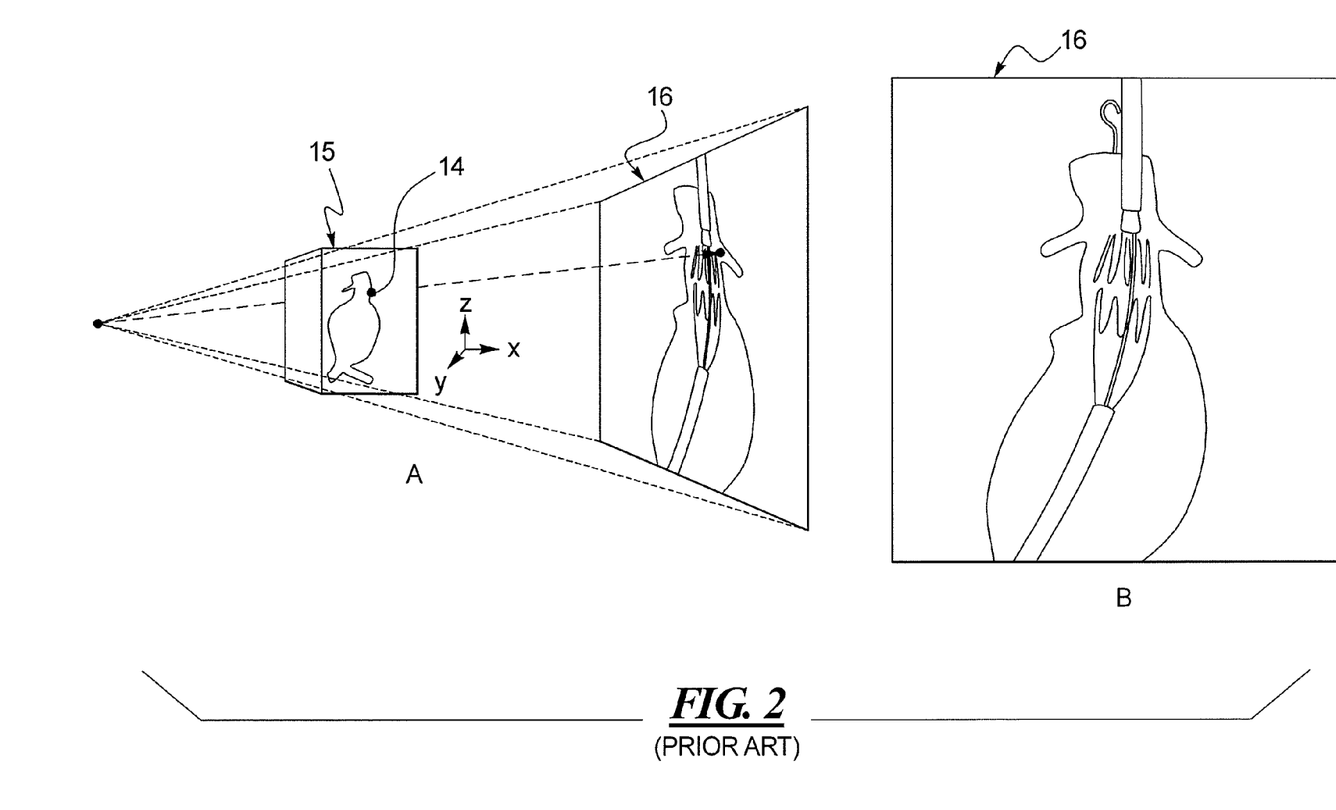

To not have to inject contrast medium permanently to control this complex stent positioning, as shown in FIG. 2A,B,C it is possible in a known method to overlay a registered 3D volume 15 showing the (segmented) relevant part 14 (aneurysm) of the aorta 11 (FIG. 1A,B,C) to guide the positioning of the stent 10 (FIG. 1). Knowing the registration of the volume 15 to the C-arm of an angiography system and the projection geometry, the volume 15 can be projected anatomically correct to the 2D fluoro (fluoroscopy) image 16 of the angiography system. See prior art FIGS. 2A,B.

Thus prior art FIGS. 2A,B show a 2D3D overlay. If the 3D volume 15 is registered to the C-Arm and the projection geometry of the C-Arm is known (FIG. 2A), the 3D volume 15 can be overlaid anatomically correct to the 2D fluoroscopic image 16 (FIG. 2B). The visualization can also follow each angle change etc. of the C-Arm.

Figure 3:
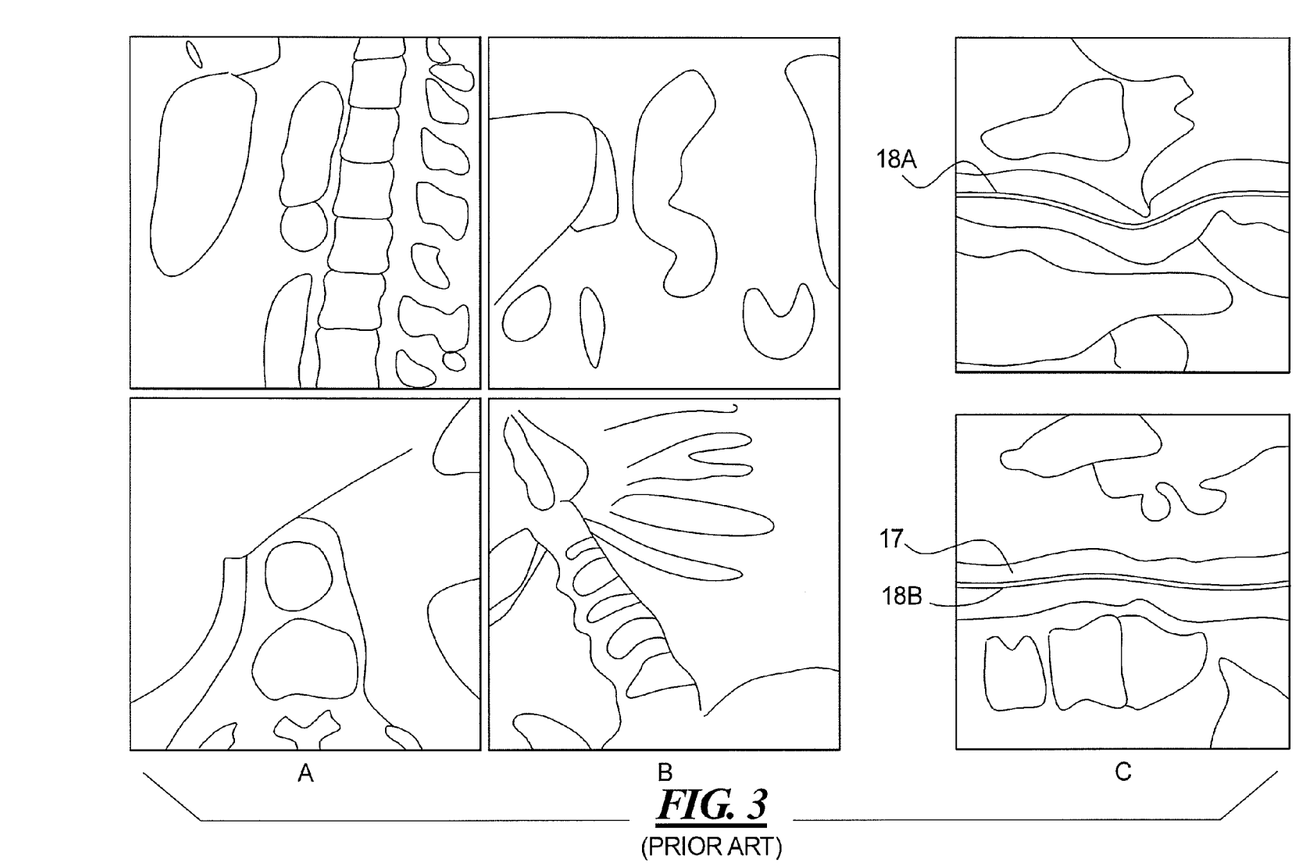

A visualization problem can be that during this overlay the aorta may look different than in the diagnostic images the physician usually uses for planning the intervention. For planning purposes, the 3D image information gets displayed as so called "Curved MPRs (Multi-Planar Reconstruction) (CPRS (Curved Planar Reconstruction))" (see Armin Kanitsar, Dominik Fleischmann, Rainer Wegenkittl, Meister Eduard Gröller, "Diagnostic Relevant Visualization of Vascular Structures", Technical Report TR-186-2-04-02, Jan. 20, 2004, TU Vienna). Prior art FIGS. 3A,B,C basically provide a standardized view on the organ by straightening the aorta 17. See prior art FIG. 3C.

Prior art FIGS. 3A,B,C thus show possibilities to visualize the aorta. FIGS. 3A, B show the "usual" way to visualize aortic angiographies, the MPR (Multi-Planar Reformation) mode—respectively a volume rendering VRT shown in FIG. 3B. Another way, especially for segmented vessels, is the display as a so called CPR (Curved Planar Reformation) which offers a rotation around the center line 18A (FIG. 3C). Sometimes the aorta 17 is stretched, so that the center line 18A becomes a straight line 18B, which provides a standardized view onto the organ (see Kanissar et al., supra).

SUMMARY OF THE INVENTION

It is an object to provide an adaption of the 2D3D overlay which reformats the 2D fluoro similar to a curved planar reconstruction (CPR). The method gives the physician a standardized view on the overlay of the segmented aorta, comparable to what is already know from diagnostic CT.

In a method for a fluoroscopy controlled insertion of a stent into a curved aorta of a patient for aneurysm repair, a 3D volume image is obtained of the patient's aorta at the aneurysm. By knowing a registration of the 3D volume image to a C-arm of an angiographic system and projection geometry of the angiography system, the 3D volume image is projected anatomically correct to a 2D fluoroscopy image of the angiography system. For the 2D3D overlay, the 3D volume image is displayed as a curved planar reconstruction in which the 2D fluoroscopy image and the 3D volume image are warped around a curved center line of the patient's curved aorta or around a curved guide instrument center line to correct for the curvature of the aorta so that the previously curved aorta center line or curved center line of the guide instrument turns into a straight line. The 2D3D overlay is used to visualize the insertion of the stent.

BRIEF DESCRIPTION OF THE DRAWINGS

FIGS. 1A,B,C show insertion of a stent graft into an aorta;
FIGS. 2A,B show a 2D3D overlay;
FIGS. 3A,B,C show various ways to visualize the aorta;
FIGS. 4A,B illustrate a first preferred embodiment with a CPR based 2D3D overlay having warping;
FIGS. 6A,B show a second preferred embodiment with a CPR based 2D3D overlay having warping;
FIGS. 8A,B,C show a direct comparison of the first preferred embodiment method and the second preferred embodiment method;
FIGS. 9A,B,C show an extension of the CPR overlay to an entire AAA segmentation.

DESCRIPTION OF THE PREFERRED EMBODIMENTS

For the purposes of promoting an understanding of the principles of the invention, reference will now be made to the preferred embodiments/best mode illustrated in the drawings and specific language will be used to describe the same. It will nevertheless be understood that no limitation of the scope of the invention is thereby intended, and such alterations and further modifications in the illustrated device and such further applications of the principles of the invention as illustrated as would normally occur to one skilled in the art to which the invention relates are included.

Two main methods are disclosed and described in the following. The methods are described for abdominal aortic aneurysms but can of course be extended to any case where CPR reformatting is usually applied, e.g. thoratic aneurysms.

Preconditions for both methods are a calibrated C-Arm Angio System (like the prior art Siemens Zee systems); and a 3D volume of the aorta which is registered to the C-Arm.

The first preferred method embodiment (FIGS. 4A,B) adapts the 2D3D overlay to the usual CPR visualizations for CT. Therefore additionally the center line 19 of the aorta 40A needs to be known. Then, because of the registration, the projection of this center line 19 onto the 2D fluoro image (curved line 19 in (FIG. 4A) is already known. Now the 2D image (respectively the combined 2D3D image) can be "warped" around the projected center line 19 to correct for the curvature of the aorta. The formerly curved center line 19 now turns into a straight line 20 (FIG. 4B) of a straightened aorta 40B. If, for example, the angulation of the C-Arm changes during the intervention, this reformatting can of course be adapted in real time.

Figure 4:
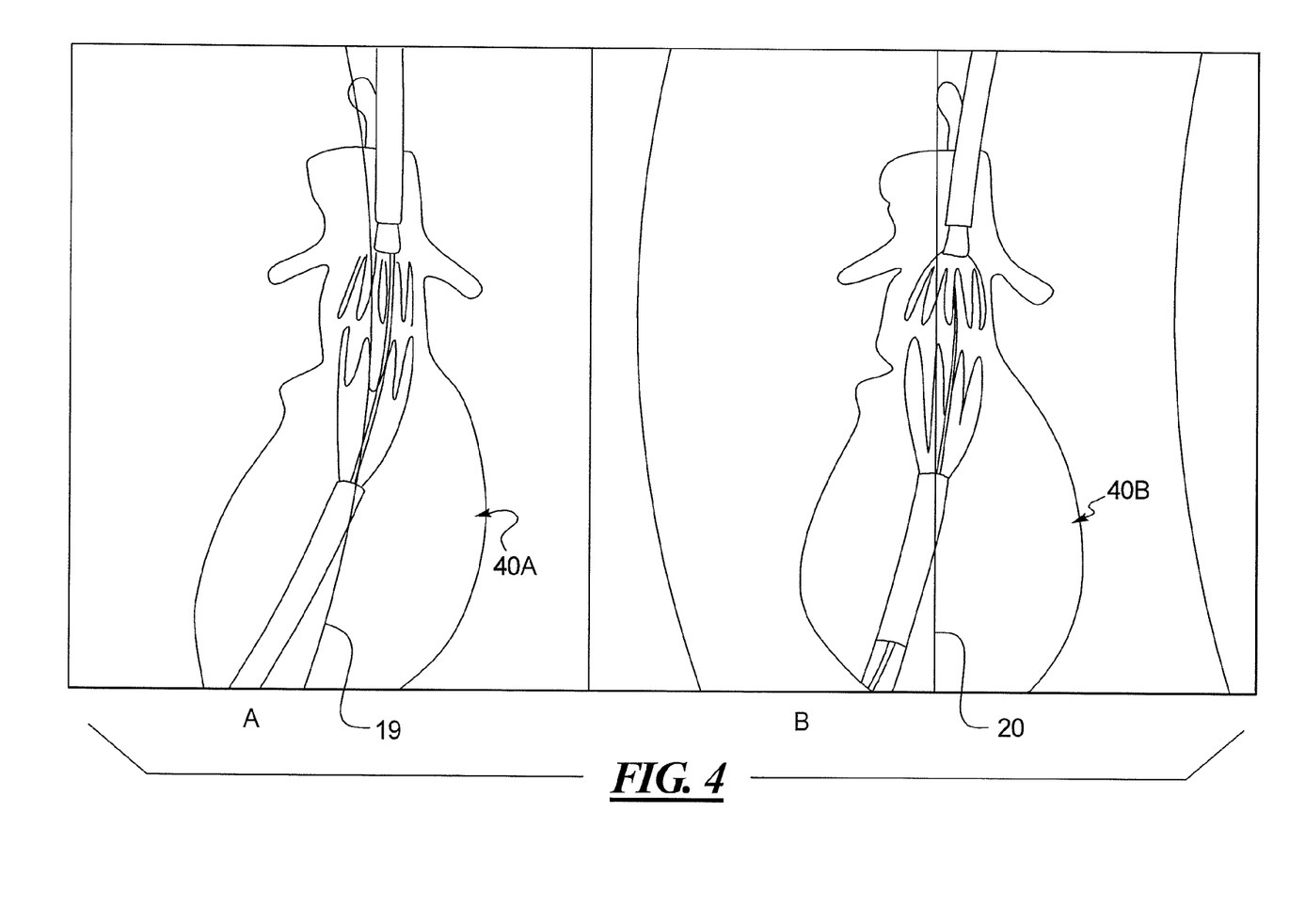

Thus FIGS. 4A,B illustrate a CPR based 2D3D overlay of the first method. They show a first preferred embodiment method wherein the physician is given a standardized view on the overlay of the segmented aorta, comparable to what is already know from the diagnostic CT.

Because of the segmentation, the center line 19 of the aorta 40A (which will be overlaid to fluoro) is known, and of course with it the projection of this center line onto the 2D fluoro image (line 19 in FIG. 4A). Instead of the "usual overlay" shown in FIG. 4A, the 2D fluoro (respectively the combined image) is now "warped" to correct for the curvature of the center line 19, so that the center line now is a straight line 20 in FIG. 4B. If e.g. the angulation changes, this reformatting can of course be adapted in real time.

Figure 5:
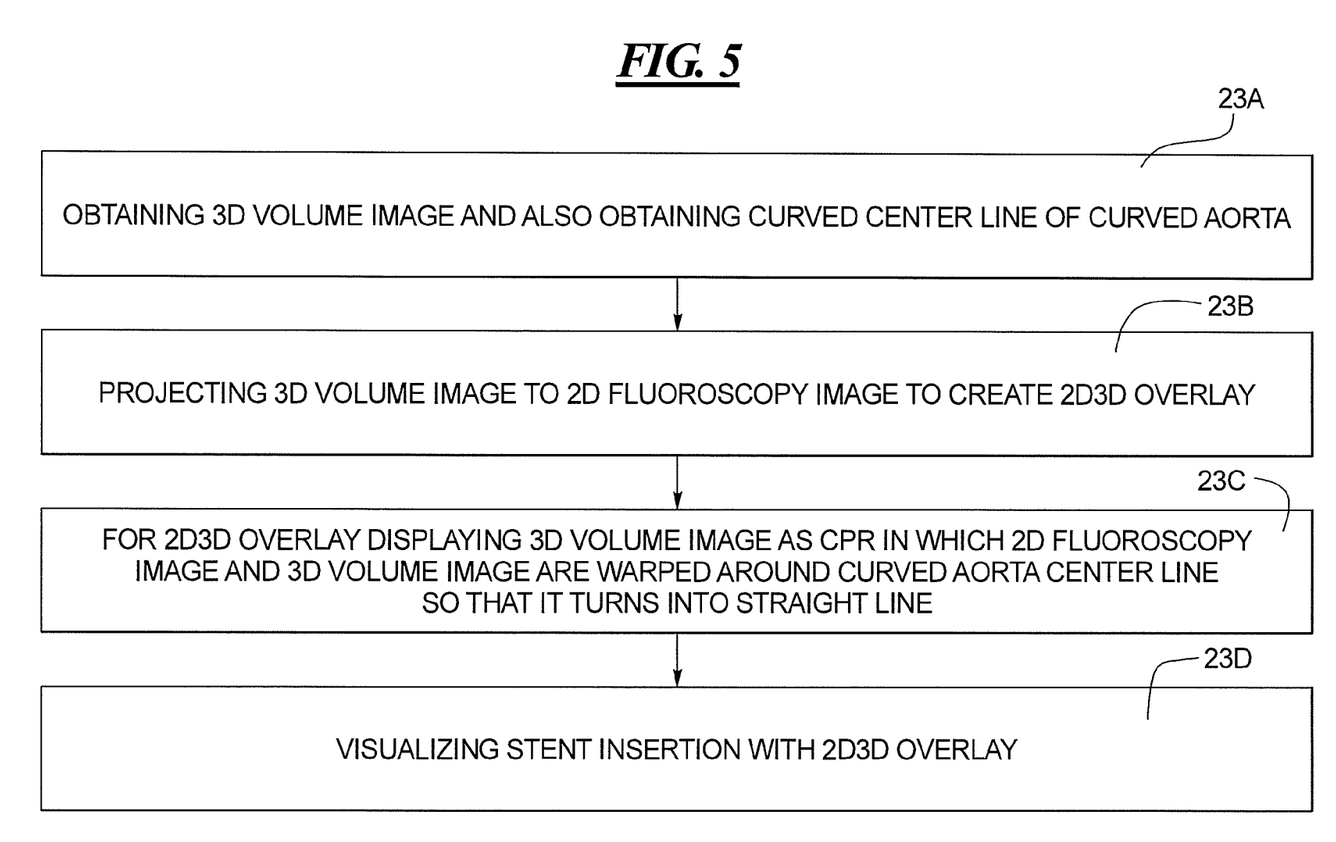
FIG. 5 is a flowchart of the first preferred embodiment method.

The flowchart of FIG. 5 shows the method for the fluoroscopy controlled insertion of a stent into a curved aorta according to the first preferred embodiment method. In step 23A a 3D volume image of the aorta at the aneurysm is obtained and also a curved center line 19 of the patient's curved aorta 40A is obtained. In step 23B, knowing a registration of the 3D volume image to the C-arm and projection geometry of the angiography system, the 3D volume image is projected anatomically correct to a 2D fluoroscopy image of the angiography system taking the fluoroscopy image of the patient during the insertion of the stent into the aorta to create a 2D3D overlay. In step 23C for the 2D3D overlay, the 3D volume image is displayed as a curved planar reconstruction in which the 2D fluoroscopy image and the 3D volume image are warped around the curved center line 19 to correct for the curvature of the aorta 40A so that the previously curved aorta center line 19 turns into a straight line 20 for a straightened aorta 40B. In step 23D, using the 2D3D overlay, the insertion of the stent is visualized with the angiography system.

Figure 6:
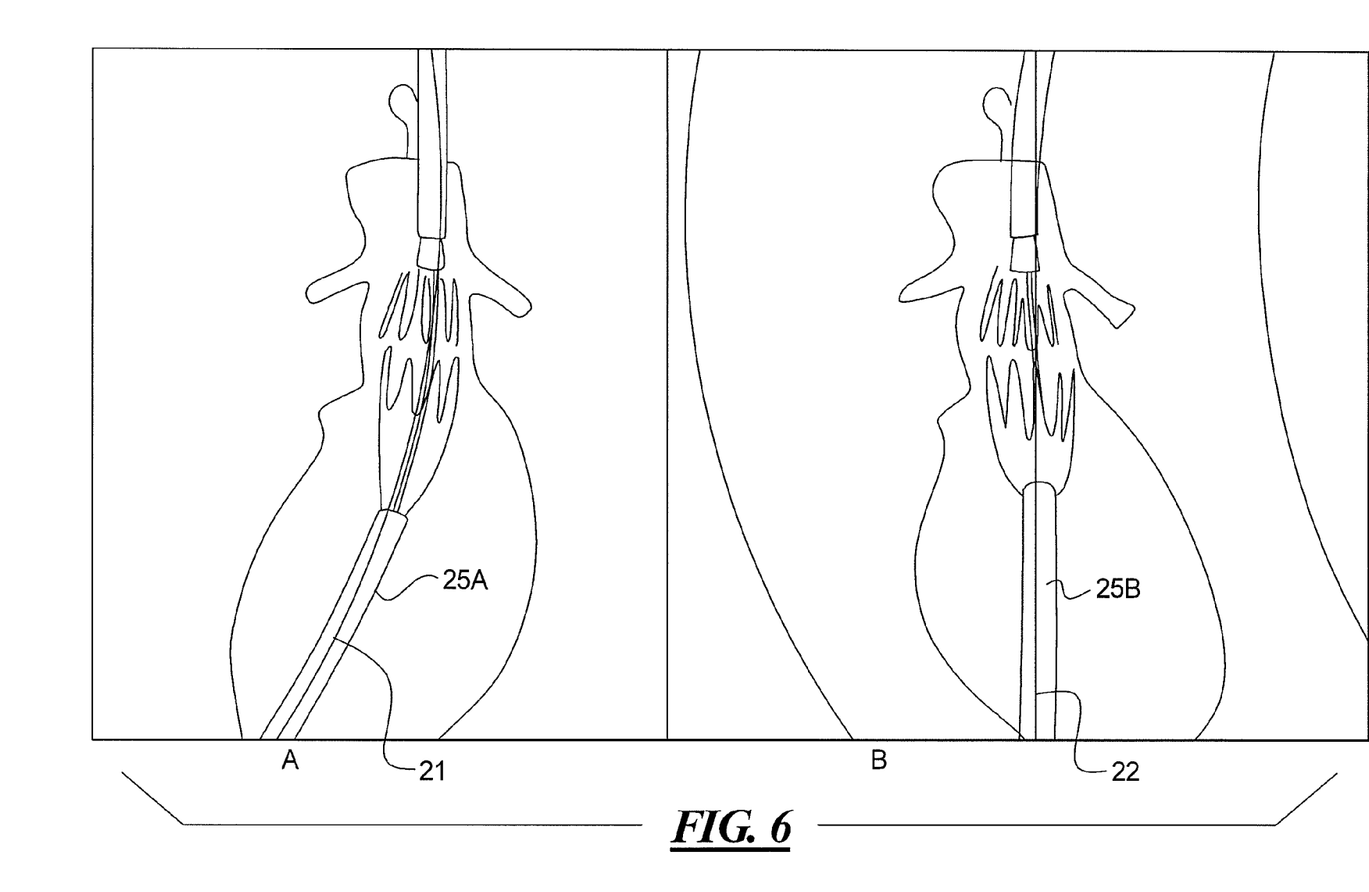

The second approach (FIGS. 6A,B) accounts for the bended guide device 25A (such as an insertion catheter 25A or a guide wire) rather than for the aorta itself but still uses a similar warping. The method is to give the physician a more precise view of the expanding stent graft. Here it is assumed that the inserted curved guide device 25A (catheter) can be recognized (and tracked) in the 2D fluoro image as curved center line 21 in FIG. 6A. Instead of the "usual overlay" shown in FIG. 6A, the 2D fluoro (respectively the combined image) is now "warped" around the line 21 which marks the detected device 25A (guide device such as a guide catheter for the stent) to correct for the curvature of the guide device 25A. The formerly curved guide device 25A (and with it the stent mounted in it) now turns into a straight center line 22 of the straightened catheter guide device 25B (FIG. 6B). If, for example, the angulation of the C-Arm changes during the intervention, this reformatting can of course be adapted in real time.

Thus FIGS. 6A,B show a CPR based 2D3D overlay according to the second embodiment method which provides for the bended guide device 25A (such as a catheter) to give the physician a more precise view on the expanding stent graft. This second method assumes the inserted curved guide device 25A (catheter) can be recognized in the 2D fluoro images and has a curved center line 21 in FIG. 6A showing the guide device as a catheter 25A. Instead of the "usual overlay" shown in FIG. 6A, the 2D fluoro (respectively the combined image) is now "warped" to correct for the curvature of the device, so that the guide device or instrument 25A is now straightened as shown at 25B where the rest of the image is warped correspondingly. If, for example, the angulation changes, this reformatting can of course be adapted in real time.

Figure 7:
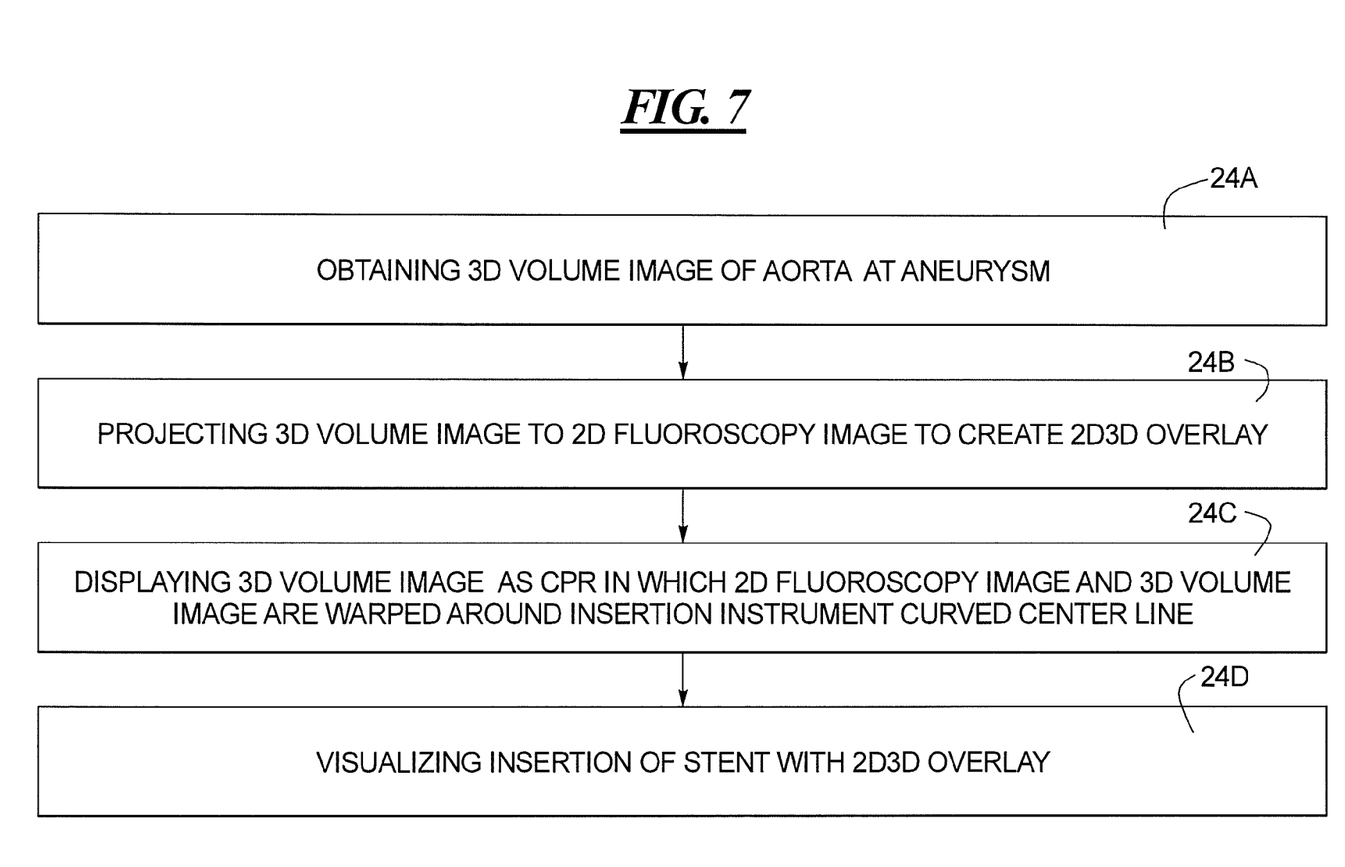
FIG. 7 shows method steps of the second preferred embodiment method.

Method steps of the second preferred embodiment will now be described with respect to the flowchart of FIG. 7. In step 24A, a 3D volume image of the patient's aorta is obtained at the aneurysm. In step 24B, by knowing a registration of the 3D volume image to the C-arm and projection geometry of the angiography system, the 3D volume image is projected anatomically correct to a 2D fluoroscopy image of the angiography system taking the fluoroscopy image of the patient during the insertion of the stent using a curved guide device or instrument 25A (catheter, for example) into the aorta to create a 2D3D overlay, the guide instrument having a curved center line 21 because of the curvature of the aorta. In step 24C, for the 2D3D overlay, the 3D volume image is displayed as a curved planar reconstruction in which the 2D fluoroscopy image and the 3D volume image are warped around the curved guide instrument or device 25A center line 21 to correct for the curvature of the aorta so that the previously curved guide instrument 25A center line 21 turns into a straight center line 22 for straightened guide instrument or device 25B. In step 24D, using the 2D3D overlay, the insertion of the stent is visualized with the angiography system.

Figure 8:
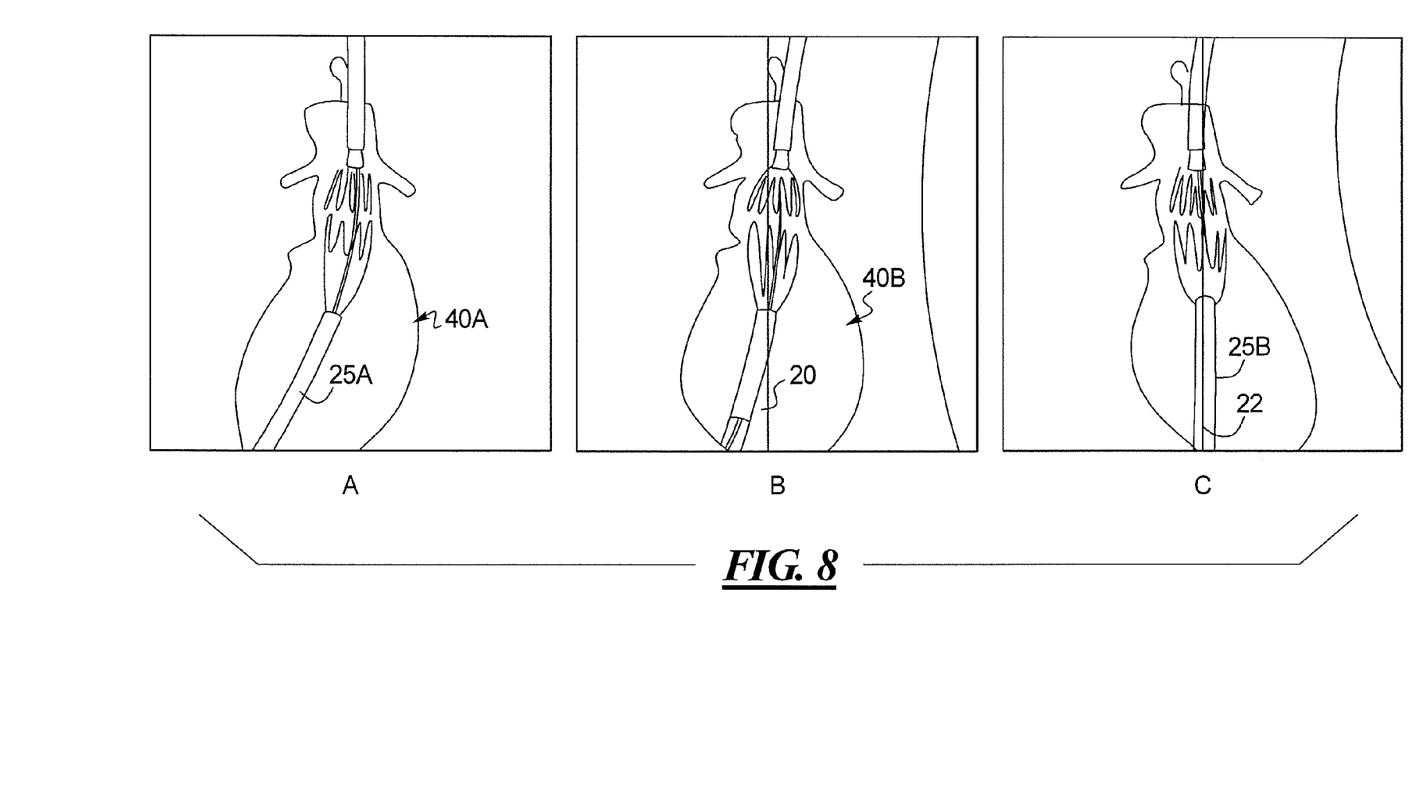

FIGS. 8A,B,C show a direct comparison of the first method (FIGS. 8A,B) and the second method (FIGS. 8A,C). FIG. 8A shows the "usual" unwarped 2D3D overlay, FIG. 8B shows the reformatting to straighten the aorta (given by the aortic center line) and FIG. 8C shows the reformatting to straighten this insertion device or instrument.

Figure 9:
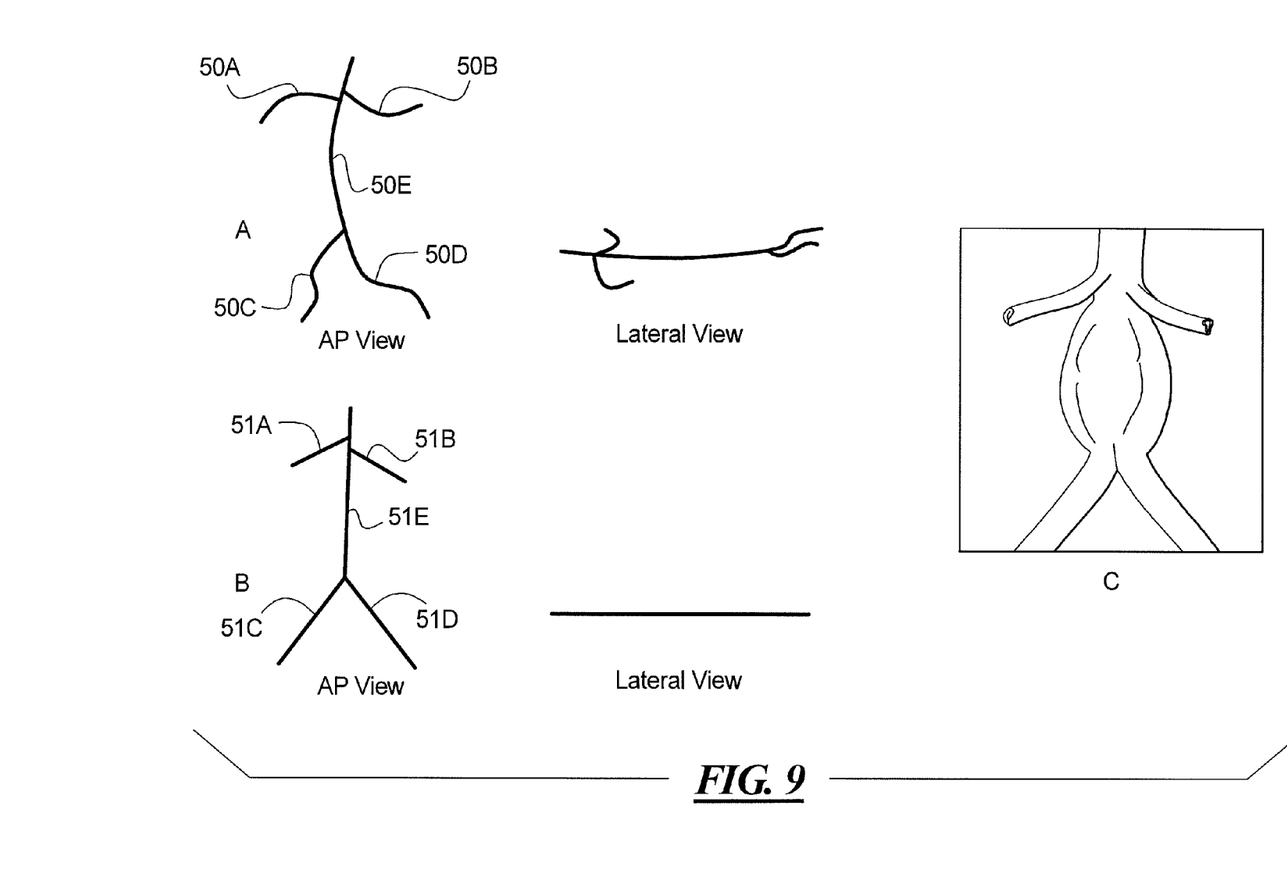

Since generally not only the center line of the aorta of the AAA will be curved and can be straightened, but also the center line of all branches will have curvatures in 3D, an extension as shown in FIGS. 9A,B,C can be applied to the above methods. Here, the method is to straighten all of the AAA center lines shown in FIG. 9A as 50A,B,C,D,E (not only the aorta 50E), to get the standardized view with straight center lines 51A,B,C,D,E shown in FIG. 9B. This requires multiple distortions of the 2D fluoro on which the 3D segmentation is overlaid but will give the physician a standardized view on the AAA during the procedure.

Thus FIGS. 9A,B,C show an extension of the CPR overlay to the entire AAA segmentation. FIG. 9A generally shows that not only the curved center line 50E of the aorta of the AAA can be curved and can be straightened, but also the center line 50A,B,C,D of all branches will have curvatures in 3D. Then with the method the concept is to straighten all of them, to get the standardized view with straight center lines 51A,B,C,D,E shown in FIG. 9B. This requires multiple distortions of the 2D fluoro on which the 3D segmentation is overlaid but will give the physician a standardized view on the AAA during the procedure.

The following advantages result from the two preferred methods. The proposed reformatting of the 2D3D overlay image allows the physician, during a 2D3D image guided procedure, a standardized view on the overlay of the segmented aorta, comparable to what is already know from the diagnostic CT.

Although preferred exemplary embodiments are shown and described in detail in the drawings and in the preceding specification, they should be viewed as purely exemplary and not as limiting the invention. It is noted that only preferred exemplary embodiments are shown and described, and all variations and modifications that presently or in the future lie within the protective scope of the invention should be protected.

We claim as our invention:

1. A method for fluoroscopy controlled insertion of a stent into a curved aorta of a patient for aneurysm repair, comprising the steps of:
   providing an angiography system having a C-arm;
   obtaining a 3D volume image of the patient's aorta at the aneurysm by use of the angiography system;
   obtaining a 2D fluoroscopy image of the patient by use of said angiography system during said insertion of the stent into the aorta;
   by knowing a registration of said 3D volume image to said C-arm and projection geometry of said angiography system, projecting said 3D volume image, while remaining anatomically correct, to said 2D fluoroscopy image of said angiography system to create a 2D3D overlay;
   for said 2D3D overlay, in order to display the 3D volume image as a curved planar reconstruction (CPR), warping the 2D fluoroscopy image and the 3D volume image around either a curved center line of the curved aorta or a curved center line of a curved guide instrument to correct for the curvature of the aorta so that the previously curved aorta center line or guide instrument center line turns into a straight line, and then displaying the 3D volume image as said curved planar reconstruction; and
   visualizing with the angiography system insertion of the stent by use of said 2D3D overlay of the angiography system.

2. A method for fluoroscopy controlled insertion of a stent into a curved aorta of a patient for aneurysm repair, comprising the steps of:
   providing an angiography system having a C-arm;
   obtaining a 3D volume image of the patient's aorta at the aneurysm and also obtaining a curved center line of the patient's curved aorta by use of the angiography system;
   obtaining a 2D fluoroscopy image of the patient by use of the angiography system during said insertion of the stent into the aorta;
   by knowing a registration of said 3D volume image to said C-arm and projection geometry of said angiography system, projecting said 3D volume image, while remaining anatomically correct, to said 2D fluoroscopy image of said angiography system to create a 2D3D overlay;
   for said 2D3D overlay, in order to display the 3D volume image as a curved planar reconstruction (CPR), warping the 2D fluoroscopy image and the 3D volume image around the curved center line to correct for the curvature of the aorta so that the previously curved aorta center line turns into a straight line; and
   visualizing with said angiography system insertion of the stent by use of said 2D3D overlay of the angiography system.

3. The method of claim 2 wherein said obtaining of said curved center line of the patient's curved aorta is obtained from said 3D volume image.

4. The method of claim 2 wherein said obtaining of said 3D volume image is with said angiography system.

5. The method of claim 2 wherein center lines of branches of the aorta are also straightened.

6. A method for fluoroscopy controlled insertion of a stent into a curved aorta of a patient for aneurysm repair, comprising the steps of:
   providing an angiography system having a C-arm;
   obtaining a 3D volume image of the patient's aorta at the aneurysm by use of the angiography system;
   obtaining a 2D fluoroscopy image of the patient by use of said angiography system during said insertion of the stent into the aorta;
   by knowing a registration of said 3D volume image to said C-arm and projection geometry of said angiography system, projecting said 3D volume image, while remaining anatomically correct, to said 2D fluoroscopy image of said angiography system to create a 2D3D overlay;
   for said 2D3D overlay, in order to display the 3D volume image as a curved planar reconstruction (CPR), warping the 2D fluoroscopy image and the 3D volume image around a curved center line of a curved guide instrument used to insert the stent to correct for a curvature of a curved center line of said guide instrument because of the curvature of the aorta so that the guide instrument center line turns into a straight line, and then displaying the 3D volume image as said curved planar reconstruction (CPR); and
   visualizing with the angiography system insertion of the stent by use of said 2D3D overlay of the angiography system.

7. The method of claim 6 wherein said guide instrument is a catheter for introducing and guiding placement of said stent.

8. A system for fluoroscopy controlled insertion of a stent into a curved aorta of a patient for aneurysm repair, comprising:
   an angiography system having a C-arm;
   said angiography system obtaining a 3D volume image of the patient's aorta at the aneurysm and also obtaining a 2D fluoroscopy image of the patient during said insertion of the stent into the aorta;
   said angiography system, by knowing a registration of said 3D volume image to said C-arm and projection geometry of said angiography system, projecting said 3D volume image, while remaining anatomically correct, to said 2D fluoroscopy image of said angiography system to create a 2D3D overlay;
   with said angiography system, for said 2D3D overlay in order to display the 3D volume image as a curved planar reconstruction (CPR), warping the 2D fluoroscopy image and the 3D volume image around either a curved center line of the curved aorta or a curved center line of a curved guide instrument used to insert the stent to correct for the curvature of the aorta so that the previously curved aorta center line or guide instrument center line turns into a straight line; and
   said angiography system visualizing insertion of the stent by use of said 2D3D overlay of the angiography system.

* * * * *